(12) United States Patent
Schultz et al.

(10) Patent No.: US 9,297,761 B2
(45) Date of Patent: *Mar. 29, 2016

(54) NANOPARTICULATE ASSISTED NANOSCALE MOLECULAR IMAGING BY MASS SPECTROMETERY

(71) Applicant: Ionwerks, Inc., Houston, TX (US)

(72) Inventors: J. Albert Schultz, Houston, TX (US);
Thomas F. Egan, Houston, TX (US);
Ernest K. Lewis, Pearland, TX (US);
Steven Ulrich, Houston, TX (US);
Kelley L. Waters, Houston, TX (US)

(73) Assignee: IONWERKS, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/092,732

(22) Filed: Nov. 27, 2013

(65) Prior Publication Data

US 2014/0084153 A1 Mar. 27, 2014

Related U.S. Application Data

(63) Continuation of application No. 13/156,111, filed on Jun. 8, 2011, now Pat. No. 8,614,416.

(60) Provisional application No. 61/352,678, filed on Jun. 8, 2010.

(51) Int. Cl.
*H01J 49/40* (2006.01)
*G01N 21/64* (2006.01)
(Continued)

(52) U.S. Cl.
CPC ............ *G01N 21/64* (2013.01); *H01J 49/0004* (2013.01); *H01J 49/0463* (2013.01); *H01J 49/142* (2013.01); *H01J 49/26* (2013.01); *H01J 49/40* (2013.01)

(58) Field of Classification Search
CPC ... H01J 49/40; H01J 49/0459; H01J 49/0463; H01J 49/0031; H01J 49/0004; H01J 49/142; H01J 49/26; C23C 14/223; G01N 21/64
See application file for complete search history.

(56) References Cited

U.S. PATENT DOCUMENTS 6,291,820 B1 * 9/2001 Hamza ................... G01N 23/22
250/282
6,989,528 B2 1/2006 Schultz et al.
(Continued)

FOREIGN PATENT DOCUMENTS

WO 2004/109254 A1 12/2004
WO 2011/033268 A1 3/2011
WO 2012/004607 A1 1/2012

OTHER PUBLICATIONS

International Search Report and Written Opinion of the International Searching Authority dated Oct. 25, 2011, for PCT Application No. PCT/US2011/039646.
(Continued)

*Primary Examiner* — Wyatt Stoffa
(74) *Attorney, Agent, or Firm* — Norton Rose Fulbright US LLP

(57) ABSTRACT

Methods and devices for mass spectrometry are described, specifically the use of nanoparticulate implantation as a matrix for secondary ion and more generally secondary particles. A photon beam source or a nanoparticulate beam source can be used a desorption source or a primary ion/primary particle source.

17 Claims, 4 Drawing Sheets

(51) Int. Cl.
*H01J 49/04* (2006.01)
*H01J 49/00* (2006.01)
*H01J 49/14* (2006.01)
*H01J 49/26* (2006.01)

(56) References Cited

U.S. PATENT DOCUMENTS

| | | | |
|---|---|---|---|
| 7,261,957 B2* | 8/2007 | Bijkerk | B82Y 10/00 250/505.1 |
| 7,629,576 B2 | 12/2009 | Schultz et al. | |
| 7,838,257 B2 | 11/2010 | Lee et al. | |
| 8,614,416 B2* | 12/2013 | Schultz et al. | 250/281 |
| 2002/0047180 A1 | 4/2002 | Rajh et al. | |
| 2003/0222212 A1* | 12/2003 | Beck | H01J 49/164 250/288 |
| 2004/0046130 A1* | 3/2004 | Rao | C04B 35/565 250/492.1 |
| 2004/0144932 A1* | 7/2004 | Murrell | H01J 37/3171 250/492.21 |
| 2005/0029448 A1* | 2/2005 | Chang | G01N 21/6402 250/292 |
| 2005/0035284 A1* | 2/2005 | Schultz | H01J 49/0031 250/287 |
| 2005/0230615 A1* | 10/2005 | Furutani | B82Y 10/00 250/287 |
| 2006/0138317 A1* | 6/2006 | Schultz | H01J 49/0031 250/287 |
| 2006/0284092 A1* | 12/2006 | Ward | G01N 23/04 250/311 |
| 2007/0205375 A1* | 9/2007 | Ward | B82Y 10/00 250/398 |
| 2008/0157665 A1 | 7/2008 | Wu et al. | |
| 2008/0264682 A1* | 10/2008 | Catron | H01L 31/1884 174/257 |
| 2009/0140137 A1* | 6/2009 | Hiraoka et al. | 250/282 |
| 2009/0189072 A1 | 7/2009 | Egan et al. | |
| 2009/0207869 A1* | 8/2009 | Dantus | B82Y 20/00 372/21 |
| 2010/0044580 A1* | 2/2010 | Boswell | H01J 27/024 250/424 |
| 2010/0051825 A1* | 3/2010 | Yamashita | H01J 27/14 250/423 R |
| 2010/0090101 A1* | 4/2010 | Schultz | H01J 49/0418 250/282 |
| 2010/0132507 A1 | 6/2010 | Perry et al. | |
| 2010/0177306 A1* | 7/2010 | Natan | B82Y 30/00 356/301 |
| 2010/0227308 A1* | 9/2010 | Hashimoto | G01N 33/6848 435/4 |
| 2010/0294926 A1* | 11/2010 | Murakami | 250/282 |
| 2012/0152735 A1* | 6/2012 | Allers | C23C 14/223 204/298.06 |

OTHER PUBLICATIONS

International Preliminary Report on Patentability dated Dec. 20, 2012, for PCT Application No. PCT/US2011/039646.

* cited by examiner

NANOPARTICULATE ASSISTED NANOSCALE MOLECULAR IMAGING BY MASS SPECTROMETERY

CROSS-REFERENCE TO RELATED APPLICATIONS

This application is a continuation of U.S. patent application Ser. No. 13/156,111 to J. Albert Schultz et al. filed on Jun. 8, 2011 and entitled "Nanoparticulate Assisted Nanoscale Molecular Imaging by Mass Spectrometery," which claims priority to U.S. Provisional Patent Application No. 61/352,678, filed on Jun. 8, 2010, both of which are incorporated by reference.

TECHNICAL FIELD

This invention relates to methods and devices for mass spectrometry, specifically the use of nanoparticulate implantation for use as a matrix for secondary ion and more generally secondary particles. A photon beam source or a nanoparticulate beam source can be used as a desorption source or a primary ion/primary particle source.

BACKGROUND OF THE INVENTION

It is well known in the literature that noble gas ions having energies in the kilo-electronvolt (keV) range, especially neon (Ne) and helium (He) ions, cannot be successfully used as primary ions for SIMS analysis of a molecular surface. Benninghoven found that when noble gas primary ions were used to perform SIMS analysis of pure amino acids, silver (Ag) surfaces, of all the many metallic and insulating substrates investigated, provided the best production of small intact molecular and fragment ions. However, the use of keV cluster ions ($SF_6^+$, $Au^{3+}$) as primary particles in SIMS, and ultimately, the emergence of the MALDI (matrix-assisted laser desorption) technique, eclipsed the use of monoatomic primary ion SIMS molecular surface analysis. Typical secondary ions desorbed in noble gas bombardment are either elemental ions or are very weak molecular ion signals from very small molecular ions (e.g. $C_2H_3^+$). Thus, the molecular analysis of a surface by He, Ne or even larger monoatomic ion or neutral atom bombardment has been largely abandoned for the last twenty five years.

Two critical technical issues limit the scientific community's ability to identify biomolecular interactions that underlie cellular function and pathophysiology. The first limitation relates to the fact that most analytical methods cannot detect and quantify a broad spectrum of biomolecules simultaneously. Current mass detection methodologies, including mass spectrometry, provide a narrow window into a small fraction of the biomolecular universe of proteins, lipids and carbohydrates. However, our very recent work has shown that the combination of MALDI-Ion Mobility-orthogonal time of flight Mass Spectrometry (MALDI-IM-oTOFMS) and laser post-ionization (POST) permit analysis of both charged and neutral proteins and lipids. This combination of technologies has the potential to expand the species detection capabilities at least several hundred-fold for lipids, peptides, and glycoforms. The second limitation relates to the fact that present-day MALDI imaging has a relatively poor spatial/volume resolution of more than 20,000 cubic microns (1000 $\mu m^2$ laser spot into a 20 $\mu m$ thick matrix layer)—mostly because the necessary matrix layer is thicker than the tissue to be analyzed. Effective monolayer scale matrices must be found. To this end we have recently demonstrated both the spatial resolution and sensitivity necessary for subcellular analysis by depositing a submonolayer of aerosolized gold nanoparticulate (Au NP) matrix on the tissue surface or by implanting a submonolayer of (1 nm) $Au_{400}^{4+}$ into a 10 nm region below the tissue surface. Both methods of Au NP deposition result in a matrix volume of less than 9 cubic microns under the 30 micron diameter pixel (laser spot). 10 $\mu m^3$ is approximately $\frac{1}{100}$ of the volume of a 30 $\mu m$ diameter cell. Protein and lipid profiles and lipid imaging were measured in both cases. Data was obtained from two sagital sections of unperfused frozen brain tissue. A DHB (dihydroxy benzoic acid) matrix solution droplet preferentially extracts water soluble blood proteins from the tissue which then dominate the MALDI spectrum. In contrast, no major blood proteins are seen from the Au NP-implanted tissue section; instead only histone and other higher mass proteins are detected. Therefore, laser imaging technologies based on Au NP implantation should be capable of achieving subcellular molecular profiling especially when coupled with post-ionization of desorbed neutrals in an ion mobility-oTOFMS spectrometer.

The implantation of cellular level mass spectrometry-based molecular phenotyping represents a transformational development in biomedical science and clinical pathology. Simple approaches, such as overlays with standard or confocal light microscopic images can change limited and slow histochemical and immunohistochemical approaches into streamlined, broad molecular phenotyping of even small or limited biopsy samples. Similarly, it will enable quantitative analysis of individual differences between cells within a tissue from animals or human subjects, such that variations between nominally similar cells can be studied and variations in populations characterized. It will effectively open a new universe of cellular proteomic and lipidomic phenotyping to rapid and sensitive quantitative analysis. Laser capture microdissection followed by MALDI-MS very powerfully profiles molecules from a group of localized cells; the MALD-POST-IM-oTOFMS biomolecular microscope could profile each individual cell within the group. This would open a new era for routine intra-cellular biochemical profiling of a cell populations in localized tissue regions for basic research, pathological analysis, and ultimately, clinical applications. What is needed in the art is increased molecular detection sensitivities for small volumes, such a single mammalian cell.

BRIEF SUMMARY OF THE INVENTION

The present invention is directed to methods and devices for mass spectrometry, specifically the use of nanoparticulate implantation as a matrix for secondary ions and more generally secondary particles. A photon beam source or a nanoparticulate beam source can be used a desorption source or a primary ion/primary particle source.

In one aspect of the invention there is an analytical instrument for the characterization and analysis of a sample comprising: a sample stage for positioning a sample; a nanoparticulate beam source positioned to deliver a nanoparticulate beam to a sample on the sample stage; a nanofocused primary particle beam source or a nanofocused photon beam source, or both, the beam source positioned to deliver a beam to the sample; and, an analyzer positioned to analyze material or photons emitted from the sample.

In one embodiment, the sample stage is an XY sample stage. In another embodiment, the instrument comprises a component selected from the group consisting of a cluster beam source, a vapor deposition system, a laser ablation system, an electrospray ionization source, a molecular beam source, an atomic layer epitaxy source, an ion beam deposition source, a Knudsen effusion cell, a magnetron sputter source, an electron beam evaporator source, an atomic hydrogen, oxygen or nitrogen source, an ozonolysis source, a plasma etching source, an aerosol generator source, and any combination thereof, the component being position to deliver material to the sample, to the nanoparticulate beam or to both.

In one embodiment, the analyzer comprises a mass spectrometer. In a specific embodiment where the analyzer comprises a mass spectrometer, the mass spectrometer is a time-of-flight mass spectrometer.

In one embodiment, the analyzer comprises a fluorescence spectrometer.

In one embodiment, the nanofocused primary particle beam source comprises a nanofocused neon ion particle beam source. In one embodiment, the nanofocused photon beam source comprises a nanofocused plasmonic photon source. In one embodiment, the nanoparticulate beam source is a nanofocused nanoparticulate beam source. In one embodiment, the nanoparticulate beam source is a nanoparticulate silver ion beam source. In one embodiment, the nanoparticulate beam source is a nanoparticulate aluminum ion beam source. In one embodiment, the nanoparticulate beam source is a nanoparticulate coreshell beam source. In one embodiment wherein the nanoparticulate beam source is a nanoparticulate coreshell beam source, the nanoparticulate coreshell beam source is a nanoparticulate aluminum/silver coreshell beam source. The instrument of claim 1, wherein the nanoparticulate beam source is an aluminum nanoparticulate coreshell beam source. In one embodiment, instrument is configured as a cluster tool, comprising 1) a discrete implantation cluster comprising the nanoparticulate beam source, and 2) a discrete desorption/analysis cluster comprising the nanofocused primary particle beam source or nanofocused photon beam source, or both, and the analyzer. In a specific embodiment wherein the instrument is configured as a cluster tool, the instrument further comprising a sample transfer mechanism coupling the implantation cluster with the desorptionianalysis cluster.

In another aspect of the invention there is a method for the collection of analytical data from a sample, comprising the steps of: adding matrix to the sample with a nanoparticulate beam source; thereafter desorbing chemical species from the sample using a primary particle beam source or a nanofocused photon beam source, or both; and, analyzing at least a portion of the desorbed chemical species.

In one embodiment, the primary particle beam source is a nanofocused primary particle beam source. In one embodiment, the primary particle beam source is a microfocused particle beam source. In one embodiment of the method, the method further comprises the step of adding material to the sample using comprising a component selected from the group consisting of a cluster beam source, a vapor deposition system, a laser ablation system, an electrospray ionization source, a molecular beam source, an atomic layer epitaxy source, an ion beam deposition source, a Knudsen effusion cell, a magnetron sputter source, an electron beam evaporator source, an atomic hydrogen, oxygen or nitrogen source, an ozonolysis source, a plasma etching source, an aerosol generator source, and any combination thereof, the component being positioned to deliver material to the sample, to the nanoparticulate beam or to both.

In one embodiment, the step of adding matrix to the sample with a nanoparticulate beam source comprises adding nanoparticulate silver ions to the sample with a silver ion beam source. In one embodiment, the step of adding matrix to the sample with a nanoparticulate beam source comprises adding nanoparticulate aluminum ions to the sample with an aluminum ion beam source. In one embodiment, the step of desorbing chemical species from the sample using a primary particle beam source comprises desorbing with a nanofocused neon ion particle beam source. In one embodiment, the step of desorbing chemical species from the sample using a nanofocused photon beam source comprises using a nanofocused laser. In one embodiment, the step of analyzing comprises analyzing with a mass spectrometer. In a specific embodiment wherein the method comprises analyzing with a mass spectrometer, the mass spectrometer is a time-of-flight mass spectrometer.

In one embodiment of the method, the nanoparticulate beam source is a nanofocused nanoparticulate beam source. In one embodiment of the method, the nanoparticulate beam source is a microfocused nanoparticulate beam source.

In one embodiment of the method, the primary particle beam source is a nanoparticulate beam source.

In one embodiment of the method, the nanoparticulate beam source is a coreshell structure nanoparticulate beam source. In one embodiment of the method wherein the nanoparticulate beam source is a coreshell structure nanoparticulate beam source, the coreshell structure nanoparticulate beam source is a aluminum silver coreshell structure nanoparticulate beam source.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
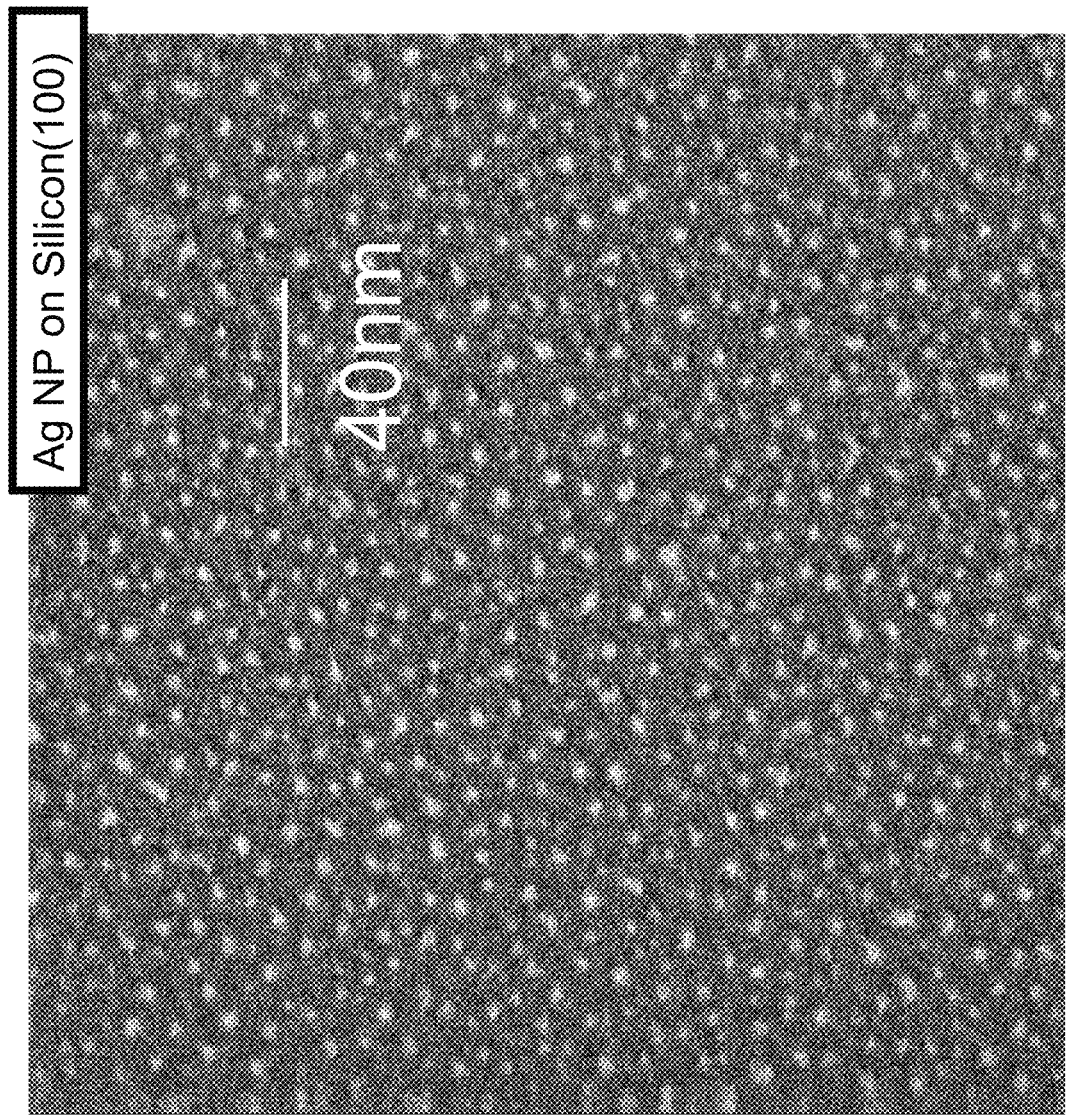
FIG. 1 illustrates a helium ion image of a silicon substrate onto which a 2 keV silver nanoparticulate beam has been impinged.

As used herein, "a" and "an" means one or more than one unless otherwise stated.

As used herein, the term "soft landed" means any ion or particle which is accelerated onto the surface with a very low energy which minimizes or completely avoids any damage to the crystallography or molecular structure of that surface.

As used herein, "IM-MS" means ion mobility mass spectrometry, which is a technique where an ion mobility spectrometer is fluidly coupled to any mass spectrometer As used herein, the term "post-ionization" means the technique of converting uncharged atoms or molecules, liberated from a surface in a SIMS or MALDI step, into ions for analysis by the application of an ionization techniques within a volume just above the surface of the sample into which the uncharged atoms or molecules have been desorbed.

As used herein, a sample denotes any material for analysis.

As used herein, the term "near surface" or "near surface region", when used in the context of a sample, is a thin top layer starting from the surface gas/surface interface layer and having typical thicknesses of about 100 nm or less which, for example, thus encompass the first several monolayers of a molecular solid.

As used herein, the term "MALDI" means matrix assisted laser desorption ionization as commonly known in the art.

As used herein, the term "MS" means mass spectrometry as commonly known in the art.

As used herein, the term "SIMS" means secondary ion mass spectrometry as commonly known in the art.

As used herein, NP-SIMS means secondary ion mass spectrometry which is assisted by implanting a NP into a sample to be analyzed for use as matrix to enhance the emission of secondary ions (and in particular molecular secondary ions) when a primary ion (which may also be a NP) is subsequently used to image the surface of the implanted sample.

As used herein, the term "TOF" means "time-of-flight" and is shorthand for a time-of-flight mass spectrometer.

As used herein, the term "oTOF" means a time-of-flight mass spectrometer having a flight tube arranged orthogonally to the separation axis of a preceding separation technique.

As used herein, "MALDI-IM-oTOF" means an instruments and methods for obtaining mobility resolved mass spectra of MALDI desorbed molecular and elemental ions.

As used herein, the term "SIMS-IM-oTOF" means an instrument and method for obtaining mobility resolved mass spectra of secondary desorbed molecular and elemental ions which are created during the bombardment of a solid by an energetic primary ion beam which impinges a surface.

As used herein, the term "LMIS" means an ion source extracted from liquid metal and can be micro or nanofocused onto a sample surface.

As used herein, the term "NP" refers to nanoparticulates, which are discrete aggregates comprising pure atoms, alloys, coreshell structures, molecular compounds or combinations thereof where the major dimension of the discrete aggregate is less than a micron and often of dimensions less than about 100 nm.

As used herein the term "nanoparticulate beam source" (or the abbreviation "NBS") means a device capable of producing on demand a flux of neutral or charged NPs which may be directed to a sample.

As used herein, the term "microfocused" when referring to a beam, means the focusing of the beam to an area of less than a mm and to about just greater than 1 micron.

As used herein, the term "nanofocused" when referring to a beam, means the focusing of the beam to an area of less than a 1 micron (µm) and to about just greater than 1 nm.

As used herein, the term "particle beam source" means a device which directs an energetic particle onto a surface.

As used herein, the term "microfocused particle beam source" means a device which directs an energetic particle onto a surface within an area of less than 1 mm and more than 1 micron.

As used herein, the term "nanofocused particle beam source" means a device which directs an energetic particle onto a surface within an area of less than a 1 micron and more than 1 nm.

As used herein, primary particle beam is a particle beam source which may be used for SIMS. This definition includes both primary ion beams and primary neutrals beams.

Reference is made herein to the terms "primary ions" and "primary particles". The meaning of primary ions should be understood to be the customary meaning in the field of secondary ion mass spectrometry. Additionally, the term primary particle also should be understood in the same context (i.e., that being of a particle, that upon impingement with a sample material, gives rise to a secondary particle). In the usual case, SIMS techniques use primary ions owing to ease of focusing of charged species using focusing electric fields, etc. However, in some cases, it is advantageous to use a neutral particle as a primary particle to impinge a sample and create secondary ions or (secondary neutral species with can be post-ionized to form ions). Thus, it should be understood that the terms "primary particles" and "secondary particles" are analogous to and correspond with "primary ions" and "secondary ions", respectively, as the latter two terms are customarily used in the SIMS literature. It merely expands the customary terms to include the use of neutral species in addition to ions. In this way, "ions" are a subset of "particles". At various points herein, the terms "primary particles", "secondary particles", "primary ions" and "secondary ions" are used, but it should be understood that they may be interchangeable, unless it is clear, either expressly or from the context, that the narrower case of ions is required rather than the broader case of particles.

The use, described herein, of nanoparticulates (NP) as a matrix for SIMS revives the use of monoatomic primary ions for molecular surfaces analysis and ultimately for molecular surface imaging. FIG. 1 shows a helium ion image of a silicon substrate onto which a 2 keV silver nanoparticulate (Ag NP) beam has been impinged using the novel nanoparticulate beam source discussed herein. The average particle size distribution is seen to be around 4 nm with some larger particles and other particles of less than 1 nm. Notably, the NPs can be located within the near surface region of a sample by a specially designed NP particle beam source either by directly accelerating the particles into a polymer surface or by first landing the NPs onto a substrate (the result of which is illustrated in FIG. 1), and thereafter adding a pure liquid analyte or analyte solution to obtain a film in which the NP are dispersed. The size and surface volume dispersion of the NP within the sample and the near surface region of the sample now becomes the ultimate determinant of the obtainable spatial resolution by microprobe or microscope based SIMS molecular mass spectrometry and other photon based imaging analysis.

Figure 2:
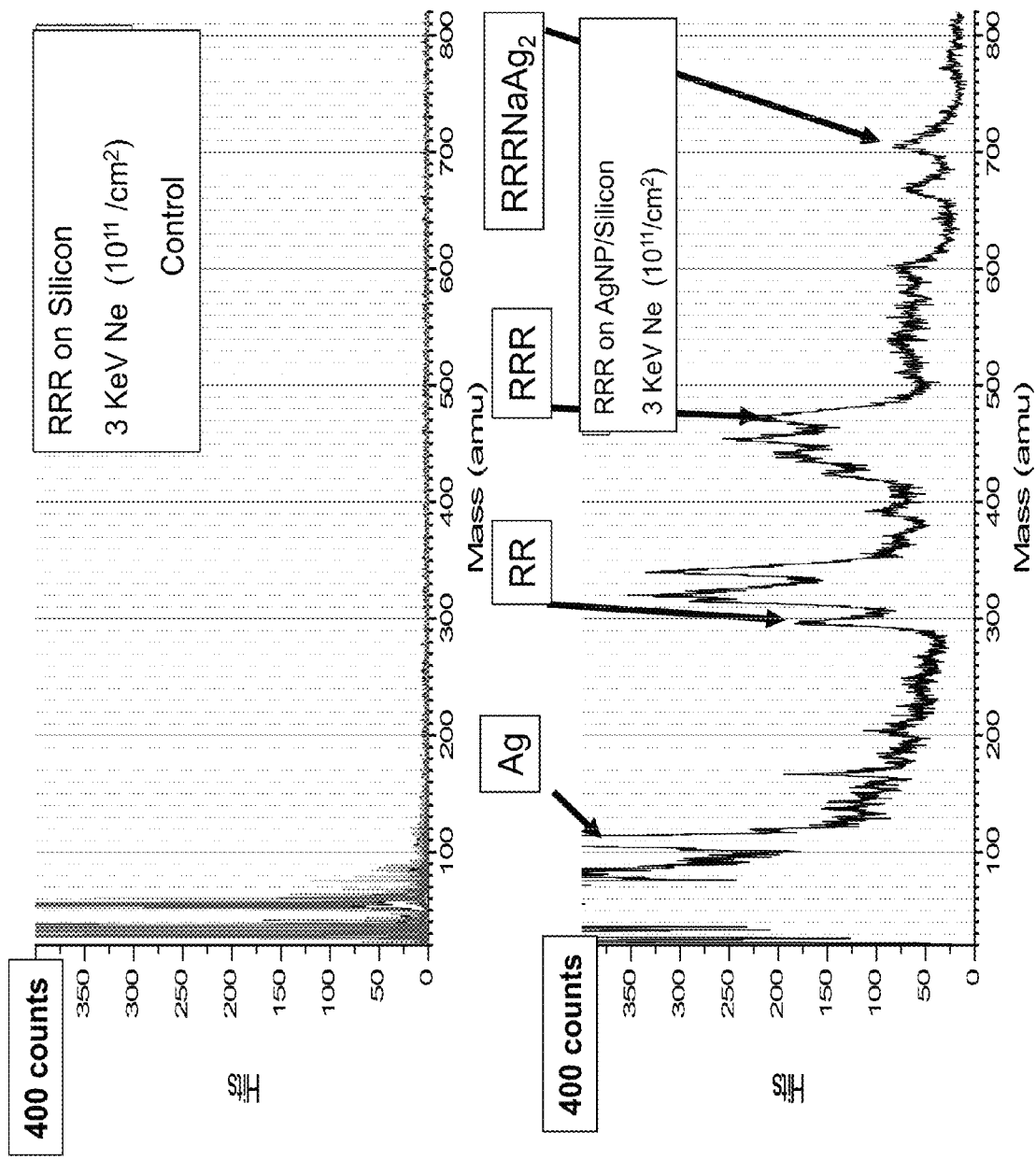
FIG. 2 illustrates comparative SIMS data for a tri-peptide film with and without Ag NP in the near surface region.

Reference is now made to FIG. 2, which shows a comparison SMIS data taken from a tri-peptide film (tri-arginine peptide (RRR)) with and without Ag NP in the near surface region. A NBS source was used to soft land Ag NP ions of average size 4 nm onto a silicon surface with a coverage of around 20% as seen in FIG. 1. A solution of peptide was deposited on the Ag NP-treated surface and the same solution was deposited onto both a blank silicon and a stainless steel surface to create a control sample of RRR without Ag NP. A control film of RRR was produced by depositing the same solution of tri-arginine onto either silicon or onto stainless steel and as can be seen, the neon bombardment produced no significant molecular ions above m/z 100. No variation of primary ion energy or fluence gave any molecular ion production from the control surface; all the secondary ions from the control surface are primarily carbon and silicon elemental and small molecular ions. By contrast, under the same bombardment conditions, the Ag NP-treated surface liberated intact RRR, Ag adducted RRR, and RR fragments. The same results could be achieved if the RRR was first added to the polymer and the Ag NP were energetically implanted into the surface.

The exemplary data was acquired using a macro-focused (100 μm diameter) 3.5 keV Ne ion beam which impinges the Ag NP surfaces onto which was deposited a 10 nmole/cm$^2$ tri-arginine peptide solution (approximately 30 nm thick). As seen in FIG. 2, a control surface produced by depositing the same coverage of tri-arginine solution onto either silicon or onto stainless steel yielded no significant molecular ions above 100 m/z when bombarded with Ne under the same conditions. No variation of energy or fluence gave any better molecular ion production than what is seen from the control spectrum. In contrast, under the same bombardment conditions, the RRR film containing Ag NP produced peaks at m/z larger than 100 including Ag$^+$ (at 107, 109), intact tri-arginine (488 amu), or structural fragments RR (loss of one intact arginine at 295). The other multiplet peaks in this mass region can also be assigned by known water or amide loss or adduction of Na either to the intact RRR or the RR themselves or to their structural fragments. The higher mass molecular peaks in the 700 range are assigned to one or two Ag atoms adducted to the RRR. Despite the measured coverage of only around 20% Ag NP by helium ion microscopy (FIG. 1), the RRR SIMS molecular ions nonetheless comprise nearly 40% of the ion intensity of the entire spectrum. The remaining ion intensity is mostly concentrated in the Ag peak (107, 109) and less so the silicon peak at 28. The peaks comprising arginine (R) fragments in the range 50-80 m/z are a minority of the total ion intensity in the spectrum. The result is data which is rich in molecular information.

Moreover, the FIG. 2 data were obtained from a convenient, but very small and non-optimal, time of flight mass spectrometer (having relatively poor sensitivity to masses above 100) whose only function was to demonstrate the efficient production of molecular ions by combining NP implantation and Ne SIMS In this so-employed primitive TOFMS, the secondary ions are extracted from the surface into a simple linear orthogonal time of flight with a flight path of 2 inches (50 mm) and a 40 mm diameter multichannel plate ion detector positioned at the first time focus. This MS has poor mass resolution of 100 at 100 amu and extremely poor detection efficiency for the high mass ions. The high voltage bias on the detector face controls the time focus and impact energy of the secondary ions onto the detector and was optimally determined to be 800 eV; for a molecule of mass 500, the ion detection efficiency is only a few percent and thus the high mass molecular secondary ions are not efficiently detected in the FIG. 2 data. If the measured ion intensities are corrected for this well-known dependence of detector efficiency as a function of velocity, then the predominance in the spectrum of the RRR and its Ag adducts are enhanced even further. It is surprising that although the Ag NP coverage is 20% and thus the Ne should on average strike (and destroy) the tri-arginine located between the NPs, molecular ions are the predominant secondary ions from this sample. The presumption is that if the Ne beam misses a Ag NP, then the beam does strike and destroy molecules (and we do measure some small elements and fragments comprising a low mass spectrum similar to that from the control). Thus, if techniques can be used which locate the position of the Ag NP so that the primary ion beam only hits the NP and not the molecular film, then we would expect to even further maximize the molecular ion intensity. If techniques for quickly locating and bombarding the NP exclusively (and thus avoiding the damage to the molecular analyte) are used, then the first and necessary step of a new approach to image the type and location of molecules within the surface by NP matrix SIMS would be achieved. Alternatively, damage to the molecular analyte can be minimized by scanning the nanoprobe particle beam or the sample (or both) in a traditional fashion while the analysis of secondary particles is resolved on a pixel by pixel basis, but when significant secondary molecular signal or NP signal is encountered, the scanning is halted at that spot to maximize molecular information. Re-application of NP after raster scanning can allow depth profiling of the near surface region.

While not intending to be bound by theory, and while the exact mechanism is not known, it is believed that a number of well understood physical phenomena contribute to these remarkable and unexpected molecular SIMS which results from Ne impinging Ag NP treated biopolymer samples of FIG. 2. Within a solid Ag surface bombarded at normal incidence by 10 keV Ne, the implanted Neon depth distribution is centered around a depth of 5 nm. By analogy if we focus a 0.5 nm spot of 10 keV Neon onto one Ag NP of 10 nm diameter (and ignore that the deposition range of Ne may be larger within a Ag NP compared to solid silver) then Ne will transfer most of its energy either through nuclear or electronic stopping processes to the Ag atoms and the Ne will remain trapped within the NP. The collision sequence of each subsequent Ne particle will cause higher and higher Ag and Ag$^+$ evaporation rates. Moreover vacancies will form within the remaining portion of the NP where trapped residual Ne gas pressure can accumulate and exert large internal forces which further weakens the intermetallic binding of the Ag in the NP and assists the vaporization of the remaining portions of the partially sputtered NP. This is in analogy to surface implantation of keV noble gas ions into metals where such phenomena are well known. Moreover, NP plasmonic effects can increase a photon absorption cross-section of the NP at a plasmon resonance which can interconvert the photon energy through three body interactions into kinetic ejection of atoms or ions. If the Ne primary ion excites this plasmon resonance, then this may be yet another way to increases the coupling of inelastic energy loss of the primary Neon ion energy into the Ag NP. Molecular SIMS with a 20 Nm Satial Resolution by Combining 10 nm NanoParticulate Deposition with 0.5 nm He or Ne or Other Nanofocused Ion or Photon Irradiation One preferred embodiment is to use the recently developed, commercially available He or Ne ion nanoprobes which can attain spatial focuses down to 0.25 nm. An experimental combination which would then define the ultimate spatial resolution of a molecular SIMS ion microprobe is as follows. In a nanoparticulate beam source (NBS), a NP ion is created and optimized for size, shape, and elemental or molecular composition and is either soft landed from the NBS onto or implanted into the surface of interest. The NBS and the surface may be in a separate chamber, or the separate chamber may contain a vacuum lock between the NBS and the ion microprobe or the NBS may be contained within or fluidly coupled with the ion microprobe itself. The partial coverage of NP actually gives fairly uniform spacing of the nanoparticulates on a variety of surfaces by a self-avoidance mechanism and this persists into the near surface region. One way to achieve nearly uniform dispersion of NP throughout the near surface region, is to use a sequence of first high energy (e.g., 10 keV) implantation of a known dosage of NP ions from the NBS, followed by a second dosage with an 8 keV NP energy so that ever shallower depths within the near surface region receive uniformly dispersed NP comprising around 20-30% of the volume. Further steps of reducing the NBS energy and dosing will sequentially fill in the remaining unimplanted volume of the near surface region until at the last a soft landing dose can be applied to the surface of the sample. At this point in the sequence, the sample will have a nearly uniform volumetric dispersion of the NP between the molecules comprising the near surface region. In practice, we have found by sputter depth profiling that the NP-implanted near surface region of a biological tissue can be uniformly implanted with NP throughout a 50-100 nm depth depending on the energy and size of the NP and the type of tissue.

Thus, the smallest pixel dimensions of any microprobe analysis based on interacting with a single Ag NP is the diameter of the NP itself, while the pitch (the unbombarded area) is the average distance between particles. For the Ag NP on silicon shown in FIG. 1. this becomes a 4 nm pixel size and about a 15 nm pitch. We now introduce a combined microprobe, combining the use of both He and Ne ions. Helium ions are far less damaging to the first 200 nm of a biological tissue than Ne for the same dose and kinetic energy. Thus it is possible, using the least destructive dose and energy He ion microprobe, to first ion etch fiduciary marks on the sample surface near the sample area of interest and then to quickly obtain a pixelated secondary electron contrast image of the position (relative to these fiduciary mark) of each Ag NP on the surface of the tissue. Once a map has been made of the location of the NP, the helium gas can be switched to Neon and by relocating the Helium ion etched fiduciaries marks, the Neon can then follow the helium ion energy map to sequentially bombard only the areas containing each of the Ag NP. One type of analysis of the material which can be very potent is of course the NP-assisted molecular SIMS. The secondary ions are generated after one or more neon gas ions strike the NP. The MS of the direct ions and any post-ionized analytes (if a laser is used to ionize ejected secondary neutrals) are then measured in an analyzer; preferably a mass spectrometer, and more preferably an IM-oTOFMS. Once the Ag NP matrix has been destroyed at each location, no more useful molecular information can be obtain and the Neon beam is ideally moved to the next Ag NP location. In this way a map of Neon ion-induced secondary molecular ion emission can be overlayed with the Helium ion map of the Ag NP locations.

Other nanofocused ion beam sources (or nanofocused photon beam sources from nanophotonic light or synchrotron radiation sources) can initiate the desirable serial evaporation of a single NP. These include, e.g., Ga, In, or Au from a LMIS. Since the LMIS focal spots are in the range of 20-50 nm, their use for NP-SIMS imaging requires the implantation of comparable diameter NPs in the range of 20-50 nm. On the other hand, nanofocused Ga and In are less than ideal for SIMS because of the quick metallic implant contamination of the impact zone which not only complicates SIMS spectral assignments but also quickly reduces or eliminates the sputter ion yield of most elements and molecules from these nanoregions as the analyzed area metalizes. However, there are other gas sources such as duoplasmatrons which can produce nanofocused beams with nearly similar focal properties as the LMIS but from a variety of gas sources including: all of the noble gases; especially useful are high currents of double and triple charged Kr and Xe, as well as nitrogen and oxygen. The higher energy attainable with a triply charged Xe is useful for sputtering the larger nanoparticulates (e.g., 50 nm or greater). This is helpful because the focus of the duoplasmatron will be less than 100 nm (although a theoretically smaller focus of 20 nm may be achieved with additional engineering). Moreover, oxygen, and nitrogen nanofocused ion beams are available from these duoplamatron sources as well which enhance the SIMS sputter ion yield. The molecular images which could be attained from such a source would be limited by a focal spot size of 75 nm, which is now being attained using Argon. However, the source is very versatile and relatively much less expensive.

The NP particle beam generated by the NBS source could itself be nanofocused into a primary particle source to be alternately used as a SIMS probe after implantation. A 2 nm Au NP can create a high sputter yield of intact molecules of m/z of 1500 when used to bombard pure films of lipids and peptides. Moreover, this yield persists after prolonged bombardment of the surface, indicating that the damage created in the sputtering event was ejected from the sputter crater along with the intact molecular ions while the remaining biopolymer around the crater remained intact. These observations led the inventors to develop a sputter profiling sequence in which a focused Au NP was rastered across, and implanted within, the near surface region below the biopolymer surface. Notably, during this raster implantation of the Au NP, a spatially resolved SIMS was acquired also. Then the implanted near surface region was further rastered with a focused pulsed laser so that the implanted Au NP, which had just yielded SIMS, was used as a matrix to liberate MALDI ions. Earlier work in this area never recognized that the implanted Au NP could function as a SIMS matrix in addition to functioning as a MALDI matrix. The use of the LMIS $Au_{400}^{4+}$ NP ion source to implant the Au NP for use as a SIMS matrix and to then immediately microfocus the $Au_{400}^{4+}$ NP ion beam for use as a primary ion to obtain a NP-SIMS image assisted by the previously implanted Au NP was never considered either.

Accordingly, what we now show is that if one first uses the NP implanter to soft land or implant a sample with a spatially distributed coverage of NPs for use as a SIMS matrix then an energetic NP can also be chosen to be used as the primary ion for generating additional SIMS information from this NP implanted surface. The same type of NP can be used both as implanted matrix and subsequently also as the primary ion, and the choice of the NP type for each role may be the same or different. The NBS allows rapid interchange between implanting one layer with one NP (e.g. Au NP) and another near surface layer with, for example Ag NP. Yet a third different NP (e.g. Al NP) might be rapidly selected and used as a nanofocused NP primary particle beam in order to obtain SIMS images from the two implanted layers by accelerating the primary NP to high keV energies and collecting the secondary ion mass spectra as a function of NP beam position. In this mode, the spatial resolution is that of the nanofocused NP beam (estimated at about 500 nm at best). However, it is well known that, if the secondary electrons are properly collected and magnified onto a position sensitive detector, then the co-incidences between the secondary ions and the electrons will be correlated from each and every primary NP ion collision with the surface (predominantly the collisions will be with the NPs distributed on the surface). Typical magnifications of up to 50 can be obtained using the secondary electrons, so a 500 nm micro-focus of the NP primary ions would be enhanced to a spatial resolution of well under 50 nm for this example. A recent SIMS microscope using $Au_{400}^{4+}$ NP as a primary ion has been constructed around such a co-incident camera detector concept; however, its sensitivity to molecular SIMS relies solely on the large molecular ion sputtering yield inherent in the collision of the primary Au NP ion with an untreated biological surface. We teach here that this methodology can be vastly improved by using an implanted NP as matrix to enhance SIMS analysis of a molecular or elemental sample followed by the use of a second nanofocused NP for use as the primary ion for obtaining. The NPs chosen as the matrix and as the primary ion need not be the same and neither must necessarily be Au NP.

We have identified another factor which can affect the microscopic trajectory of any of the above listed primary ions as they near the surface. The charge on the primary ion will induce surface dipoles in the implanted NPs as the negatively charged primary NP (or positively charged $Ne^+$ or $Xe^{+3}$) nears a sample which has been prepared with closely dispersed and disposed NP implant. In the case of the negatively charged NP, there are at least two induced dipoles one on the primary particle and one on the many partial dipoles distributed on the surface NP particles closest to the point of ion impact. As the primary ion gets very close to the surface the induced dipoles in the implanted NP can guide the primary ion toward the implanted nanoparticulate which is closest to the approaching primary NP. In this way the primary NP preferentially hits the implanted NP. This focusing effect is maximized as the energy of the primary particle is lowered. Also in the case of $Xe^{+3}$, the multiple charge can create multiple holes (i.e., positive charges) within the implanted matrix NP by stripping multiple electrons from NP as the $Xe^{+3}$ approaches, and just before colliding with the surface. This imparts around 100 eV of potential energy into the matrix NP. The dipole steering of multiply charged keV-energy, monoatomic ion towards a particular implanted metallic NP, and the amount of potential energy dumped into that particular NP is enhanced as the charge multiplicity on the monoatomic ion increases. Monoatomic ions with charged states of approximately e.g., $Au^{+69}$ or higher which contain on the order of hundreds of keV of potential energy can be prepared with special ion sources and have been used to liberate intact peptides from surfaces. These intact peptide ions are not desorbed by the collision of the multiply charged primary ion, but by the potential energy and subsequent coulomb explosion by mutual repulsion of positively charged surface ions which ensues as electrons are locally removed from atoms and molecules on the surface, to fill the deep potential wells of the approaching and nearly naked multiply charged ion.

Thus NP SIMS can be usefully attained when the primary ion is a highly charged monoatomic ion which transfers potential and not kinetic energy directly to a specific implanted metallic NP which subsequently explodes and carries away surrounding molecules from the surface into the gas phase. The preferential electron extraction from the implanted metallic NP is logical for two reasons: 1) the multiply charged primary ion is going to be closer to the surface NP than to any other molecule on the surface and 2) it is much easier for an ion to obtain an electron from the energetically and spatially available electron energy bands in the metallic NP compared to the tightly bound valence electrons of a covalently bonded molecule. Thus for example if Ag NP were used as the implanted NP SIMS matrix then multiple $Ag^+$ ions would be created and desorb violently in one concerted motion which would lift molecules which were nearby. If these molecules contained double bonds or aromatic substituents then the $Ag^+$ would form a radical cation directly with these molecules to form analytically useful secondary ions. Nano-imaging could be achieved by rastering a nanofocused multiply charged primary ion as well as using a position and time focusing camera detector to measure the time and spatial origin of secondary electrons or secondary hydrogen ions from the surface in co-incidence with the other positive and negative secondary ions.

The NBS can Create and Surface-Modify Unusual NP Matrices for Gas Phase Implantation Newer and even more effective monolayer scale matrices must be found for polymer and molecular analysis of complex molecular surfaces. Recent commercial developments of NP sources based around RF magnetron provide much flexibility in the creation and manipulation of NPs. For example, not just Au NP, but any metallic or metal alloy, can be converted into NPs which have, for example, a 4 nm diameter with a range of cluster sizes between 2 and 6 nm full width half max.

The mean diameter of these particle size distributions can be shifted, for example, between 3 and 15 nm depending on source parameter. Larger particle sizes are possible as well. In fact, the particle size can be precisely tuned by varying power and gas flow rate to achieve +/−10% FWHM particle size distributions centered around a mean value which can be selected, for example, within the range of 1 nm up to 20 nm.

Figure 3:
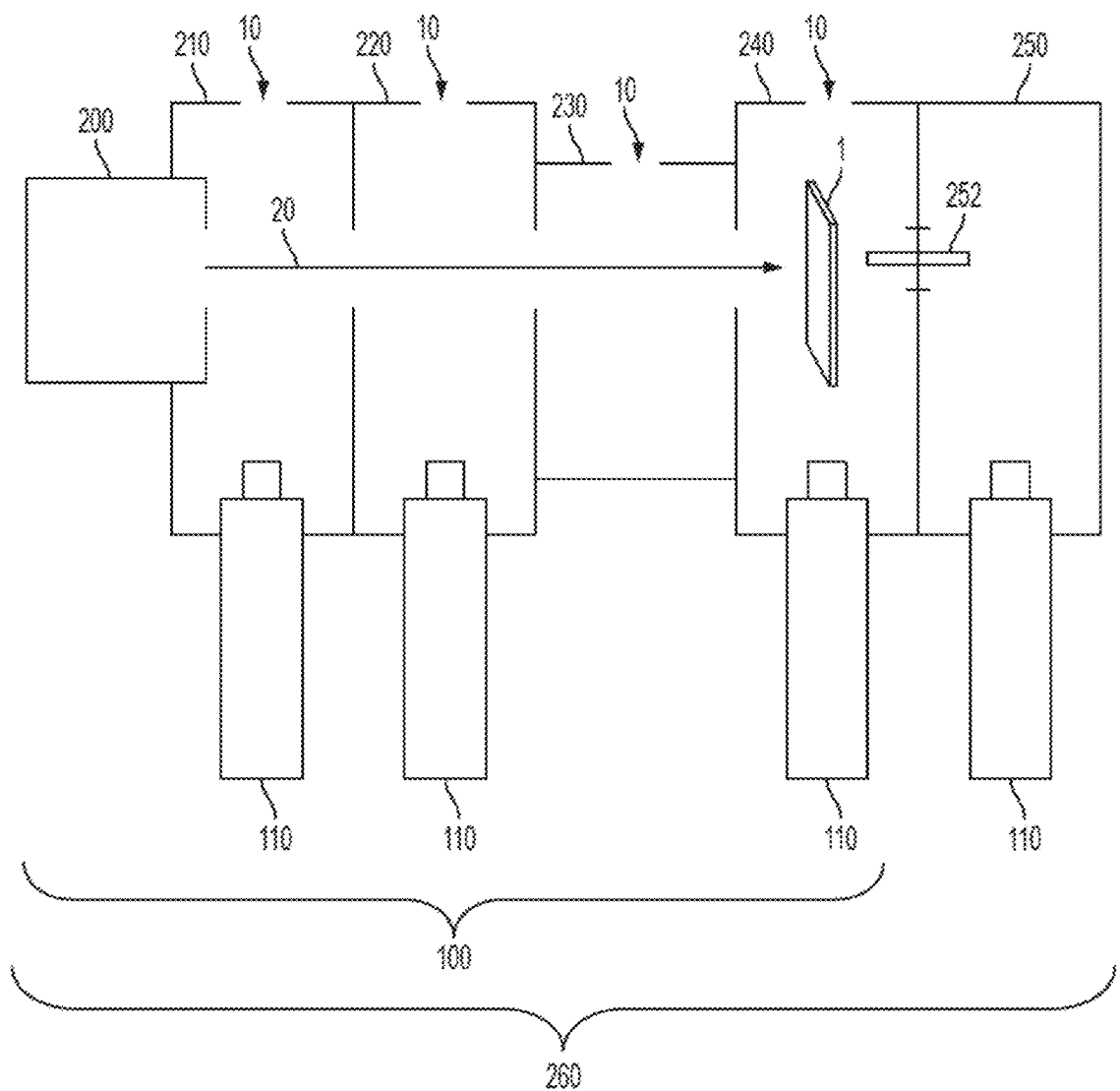
FIG. 3 is a schematic diagram of a nanoparticulate beam source.
Figure 4:
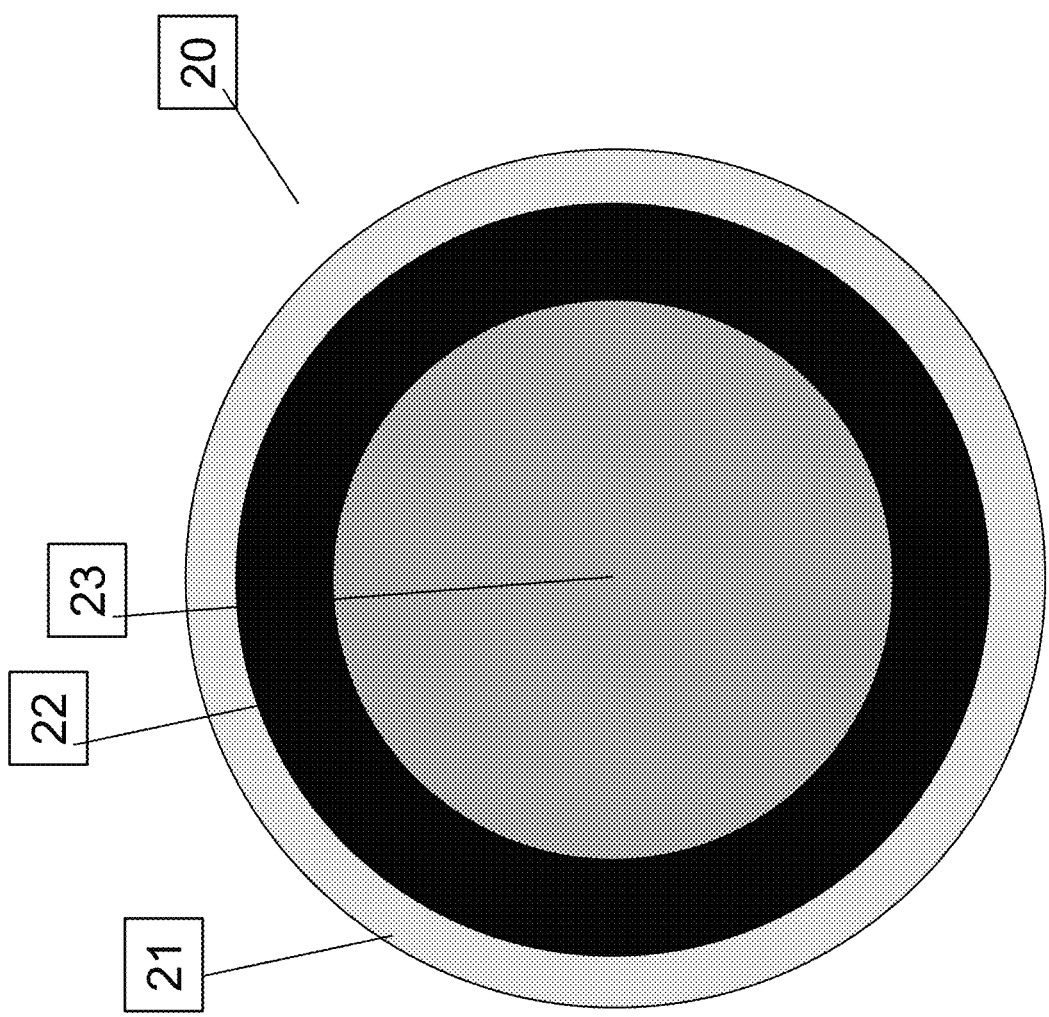
FIG. 4 is a schematic diagram of a coreshell NP structure.

One embodiment of our NBS (100) is shown in FIG. 3 and combines magnetron based NP source (200) which produces negatively charged NP (20) which are guided through a series of differentially pumped (10) vacuum regions which house ion mobility ion trap growth section (210), a beam cooling region (220), a beam acceleration and focusing section (230), and a sample chamber (240) which may also house all the sample analysis instrumentation as well. Note that multiple deposition sources (110) can be attached to each of these sections (210, 220, 230, 240) to add material to the surface of the NP (20) as they emerge from the NP source (200). The selection of multiple deposition source (110) in each of the three regions may be different from region to region according to the needs to treat the NP particle at each location. The types of material deposition sources are chosen from the group from the group consisting of a cluster beam source, a vapor deposition system, a laser ablation system, an electrospray ionization source, a molecular beam source, an atomic layer epitaxy source, an ion beam deposition source, a Knudsen effusion cell, a magnetron sputter source, an electron beam evaporator source, an atomic hydrogen, oxygen or nitrogen source, an ozonolysis source, a plasma etching source, an aerosol generator source, and any combination thereof, with the component being positioned to deliver material to said sample, to the nanoparticulate beam or to both.

Al, Ag or Au NP implantation works very well in this NBS (100) without further addition of material. However, the capability to try various other metal NP combinations is equally compelling. Au is relatively inert and does not affect the molecular ions nor does it form stable metal adduct ions (although the stable neutral Au, by adducting with other molecules, can have a profound effect on post-ionization of neutral molecule Au complexes). Other metals behave differently such as silver which makes a strongly charged Ag adduct ion (and neutral adducts as well) to many molecules. Mixing NPs or alternating deposition of two different metal NP types in between imaging raster scans can be a tool for producing desired effects on the surface including fragmentation or ionization of previously undetected molecules. The power of the NP implanter can furthermore be augmented by co-deposition of a few monolayers of traditional organic acid matrix (or other desired acid or basic additive(s)) which can chemically ionize independently of the effect of the chemical characteristics of the NP.

The above approach is a significant alternative to liquid droplet matrix deposition schemes which are plagued with unavoidable effects of fluid physics which are common to any droplet deposition technique. If one wants to achieve droplet sizes approaching 25 μm, then the evaporation rate is so high that the viscosity of the solute laden droplet rapidly increases and rapid crystallization of the matrix occurs on a time scale too fast to allow solvent extraction of surface molecules into the crystal before it is dried. Moreover, it takes several hours to deposit the matrix mixture onto the tissue even at 50 micron droplet sizes using ink jet printer technology.

An alternative is found by using the NP implanter is to decouple the addition of NP matrix, solvent (if solvent is even necessary) and acid deposition into three different sources. Multilayer liquid phases of solvents such as water may comprise only a few monolayers of fluid onto the surface. This "solvent" thickness can be controlled by temperature and water vapor pressure, whereas acid or base can be independently added from a gas effusion source during the time that the NPs are being soft landed or implanted. Moreover, this procedure can be carried out simultaneously on multiple sagital sections as previously mentioned. These different types of sources, such as Knudsen effusion cell, controlled reactive or inert gas flow, sputter deposition sources, laser deposition sources, plasma treatment, reactive gas etching, reactive ion or metastable atom surface treatment are well known within the film growth and molecular beam epitaxy community. Surprisingly, this technology has never been systematically applied to matrix deposition of mixed thin films onto biological or synthetic polymer surfaces. The molecular analysis of these hugely important classes of materials has lain dormant as a result.

Another possible combination for the sequential or simultaneous application of multiple thin film components using multiple cells for deposition onto a complex molecular surface is 1) NP implantation, 2) gas adsorption (e.g., $NH_3$, $H_2O$, $SO_2$, $NO_2$, $O_2$, $CO_2$, ozone, HF, HCl, HBr, or HI, Iodine, or volatile organic acids such as acetic acid, volatile organic bases such as ethanolamine, 3) ion or elemental addition to improve ionization efficiency or cationization efficiency such as any alkali or second row alkaline earth (e.g. Ca) which can be provided as pure neutrals by dispenser sources, or as ions by surface ionization sources, 4) non volatile additive which can be applied in aerosolized form through a droplet source, 5) volatile organometallic compounds. The sequential or simultaneous addition of elements or molecules from any of these sources can be monitored and controlled through many of the known metrologies in thin film growth which measure the incident flux of additive elements or molecules toward the surface or detect surface film growth and these include, but are not limited to: 1) capacitance manometer 2) fast ion gauges, 3) crystal microbalances, 4) mass spectrometry of surface or gas phase compositions, 5) light scattering, 6) electron or photon spectroscopies or spectrometries including ellipsometry or other interference based film thickness measurement techniques, 7) fast current measurement of ion beam flux toward the sample or into the sample.

Optimization of the NP composition and growth process as a function of NP type and size is now possible. Non-limiting elements for consideration include Li, Be, B, C, N, Na, Mg, Al, B, Ti Ag, Au, Cu, Zn, Zr, Fe, Mn, Mo, Co, V, Pt, Ni, Cr Ir, Bi, Pb, and alloys of these metal NPs. The size at which these NPs are most efficient typically varies from 1 nm up to 200 nm. In the case of plasmonic NPs such as Ag NP, the additional combination of extensive Surface Enhance Raman Spectrometry (SERS) is possible which yields structural information about molecules which are on or close to the Ag NP and may be possible also with Al NP and other more reactive plasmonic metals. The Raman spectrum can be non-destructively obtained after the addition of the Ag NP but prior to the ablation of the surface into the mass spectrometer (with ions of Ne or He or Ar or Xe or by another large NP or by simultaneous laser assisted ion bombardment, or by laser desorption alone). Similar advantages from the size engineered NPs may confer to fluorescence microscopy as well.

Coreshell NP can be Constructed to Maximize Optical Absorption and Minimize Destructive Heat Transfer to Analyte Molecules FIG. 4 shows a NP (20) which is made up of a core (23) metal and a shell structure (22). Such a structure is called a coreshell NP. The shell can often have a third layer (21) which may be a desirable (or undesirable) oxide layer for example. In the case of AgAl NP coreshell the Ag core is surrounded by an aluminum shell, but the aluminum shell may also have a thin layer (21) on its own surface which is often an oxide layer. Such an outer oxide layer is also almost always the case for pure Al NP where the center is pure Al and a thin oxidation layer is present on the surface. In some cases it is desirable to form this oxidized layer since the oxide is a thermal insulator. If Al NP is used as a SIMS or a MALDI matrix, the thermally insulating oxide structure holds the heat in the center of the particle thus preventing unwanted thermal degradation of the surrounding analyte. In many methods of NP formation, the oxide layer on such active metals is unavoidable.

The NBS (100) can control a coreshell structure in an unprecedented way since all of the vacuum regions can be made from UHV compatible materials which eliminate or reduce the presence of oxygen or water. Thus, if oxidation is desired then ozone or oxygen gas can be presented to the pure gas phase NP as it exits the NP source (200); however, if the aim is to prevent the oxidation then this can be done as well by putting the appropriate deposition source (110) into the region (210) just as the particles are exiting the NP source or in region (220) where the particles are being spatially trapped.

For example, Al can form an extremely thermally non-conductive nitride layer which also is extremely hard, is a chemically inert surface and is a wide bandgap material which is transparent to UV and VUV photons. If a high fluence atomic nitrogen source (110) is used in the NP source exit region (210) a nitride layer could be formed on top of the pure Al NP. Theoretical predictions of the influence of Al NP size on its optical absorption show that as the size if varied from 100 nm down to 10 nm its optical absorbance maximum varies from a broad absorbance which is partly reflective between 300 and 150 nm to a narrow plasmon absorbance which is centered at 150 nm and predicted to have very little component of reflectivity. Thus if we created a pure Al NP of 10 nm diameter and put a thin AlN "greenhouse" shell around this pure particle before it could oxidize then we have a AlN NP structure which could be highly useful in localizing heating into the interior of the Al core by the fluorine excimer wavelength of 157 nm. The 157 nm photon could get through the nitride layer but the ensuing heat from its absorption by the Al core could not get out. Moreover, the tensile strength of the coating would tolerate an increased internal pressure so that when the particle began evaporating it would do so forcefully and quickly. A similar mechanism would also be anticipated by Neon (or even He) bombardment. The aluminum nitride coating is radiation hard so the fast noble gas ion would create little damage as it penetrated the outer nitride layer and then dump all its kinetic energy into the pure Al center and the AlN shell would locally contain the heat. Aluminum coreshell structures, whether oxide or nitride, could auger not only advances in using excimers and ions for molecular surface analysis, but might give advantages in aspects of excimer laser surgery. Similar nitrogen, oxygen, and carbon surface chemistry of the shell or core structure can be achieved with boron nitride, carbide coatings, titatnium nitride, titanium oxide, silicon nitride oxide and carbide. An especially good guide for these types of chemistry is to look to the semiconductor industry for the processes and materials which they use to create metallic conductors on insulator, for techniques and materials to create existing and state of the art structures, transistor drain and gate features, diffusion barriers. Any materials and deposition technologies used by the semiconductor industry would be entirely compatible with NBS (100) for creating similar gas phase complex NP structures.

Additionally, when the small Al NP structures are optically excited in the UV and VUV, good energy transfer to naturally occurring fluorophores in biological structures has been shown theoretically. The search for a metal NP plasmonic alternative to synthetic labeling of biomolecules with large fluorescent dye molecules in biological systems is being actively pursued. Thus, the capability of the NBS (100) to locate specially prepared unlabeled NP fluorescent donors into biological surfaces for exciting the intrinsic fluorescence of biomolecules could provide dual use for this instrument. Alternatively, these NP probes could have use in confocal microscopy and fluorescence microscopy. One set of experiments would be to implant a NP which is designed for these optical techniques and is also an efficient SIMS or MALDI NP matrix. Then the non-destructive optical imaging could be performed, and then the molecular map determined by either nano-SIMS or nano-MALDI.

Other NP or coreshell NP structures which form strong plasmons but which are prone to oxidation (Li, Na, Mg, Al, Si) can be protected by shell coatings which are impervious to oxidation. If the NP implant is designed carefully, there can be a metallic coreshell particle with a metallic or semiconducting core and inert outer shell such as Au NP and particularly Pt NP which is impervious to surface reactions and to inter-diffusion of elements even such as hydride ions into or out of the shell.

NP Interior can be Loaded with Reducer or Oxidant (e.g., O or H)

Mg NP and MgNi NP should absorb extremely large amounts of hydrogen interstitially. An atomic H source can be used to provide the H to the pure metal or metal alloy NP prior to adding a capping shell layer. Using a Pt or Au vapor produced with a magnetron or evaporation source to coat the NPs is now possible. Another example of such a useful particle might be a Si or SiH core with a Pt/PtSi shell. Silane gas is extremely useful for silicon atomic layer eptiaxy and the Platinum Silicide is an extremely good diffusion barrier. Lithium aluminum hydride is a known reagent in organic chemistry which can only be prepared and used stably in ether could be capture in a coreshell structure and delivered unreacted to a sample surface. Mg can similarly be used as a Grignard reagent. Lithium Aluminum Hydride and $NaBH_4$ are well known reducing agents and can be encapsulated within the core of a core shell NP. All of the Group IA and Group IIA metals such as lithium or magnesium can be incorporated either directly onto the sample surface or isolated with the core of a NP coreshell structure by getter sources or by ion sources. Copper lithium alloys are amenable to coreshell incorporation.

Another useful feature of the NBS (100) especially in the ion mobility trapping region (210) or cooling region (220) would be the association of large organic molecular ions which can either be prepared and introduced with an aerosol generator or electrospray ionization source (110) with trapped NP. If the NPs are held long enough the production of substantial numbers of twinned NPs begin to dominate the gas phase NP composition. Any large molecule (either charged or uncharged) can quickly find a NP twin partner in this region and the resulting NP multimer will remained charged and can thus be implanted even within a small region onto the sample. Non-limiting examples of these types of organic molecules would be enzymes such as lipidases, proteases, fluorescent probes, drug molecules, any isotopically labeled biomolecule to be applied as a calibration standard, organic matrix molecules.

The NBS (100) can be incorporated directly into analytical tools such as a fluorescence microscope, a mass spectrometer, a confocal microscope, electron microscope etc or it can be used in conjunction with any of these instrument via being part of a cluster tool—i.e., a collection of instruments which pass a sample (by vacuum interlocks and manual or automated sample transfer devices) from one processing or analysis station to another. A particularly powerful cluster tool for biological tissue preparation and imaging by multiple techniques would be one which starts a tissue sample from the tissue cryotome where the tissue sample is prepared and mounted on cooled sample mount where it then transfers under controlled atmosphere and controlled cold temperature (so that it never warms) successively from one analytical station to the next. The NBS and the MALDI-IM-oTOFMS would be one of such stations.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An analytical instrument for the characterization and analysis of a sample comprising:
    a sample stage for positioning a sample;
    a nanoparticulate beam source positioned to deliver a nanoparticulate beam to a sample on said sample stage to deposit a matrix in the sample;
    wherein the nanoparticulate beam source comprises a nanoparticulate silver beam source or a nanoparticulate silver ion beam source;
    a nanofocused primary particle beam source, said nanofocused beam source positioned to deliver a beam to said sample including the matrix; and,
    an analyzer positioned to analyze material or photons emitted from said sample;
    wherein said nanofocused primary particle beam source comprises a nanofocused neon ion particle beam source.

2. The instrument of claim 1, wherein said sample stage is an XY sample stage.

3. The instrument of claim 1, wherein the analyzer comprises a mass spectrometer.

4. The instrument of claim 3, wherein the mass spectrometer is a time-of-flight mass spectrometer.

5. The instrument of claim 1, wherein the analyzer comprises a fluorescence spectrometer.

6. The instrument of claim 1, wherein the nanoparticulate beam source is a nanofocused nanoparticulate beam source.

7. The instrument of claim 1, wherein the nanoparticulate beam source is a nanoparticulate coreshell beam source, wherein said nanoparticulate coreshell beam source comprises a beam source of nanoparticles having a silver core surrounded by a shell of a second different material.

8. The instrument of claim 7, wherein the second material comprises aluminum and aluminum oxide.

9. The instrument of claim 1, wherein said instrument is configured as a cluster tool, comprising:
   1) a discrete implantation cluster comprising said nanoparticulate beam source, and
   2) a discrete desorption/analysis cluster comprising said nanofocused primary particle beam source or nanofocused photon beam source, or both, and said analyzer.

10. The instrument of claim 9, further comprising a sample transfer mechanism coupling said implantation cluster with said desorption/analysis cluster.

11. The instrument of claim 1, wherein said nanoparticulate beam source is a nanofocused nanoparticulate beam source of ternary coreshell nanoparticulates.

12. The instrument of claim 1, wherein the nanoparticulates from said nanoparticulate beam source are modified nanoparticulates, such that the nanoparticulate beam source comprises Ag—Al—$Al_2O_3$ ternary coreshells.

13. A method for the collection of analytical data from a sample, comprising the steps of:

adding matrix to the sample with a nanofocused nanoparticulate silver beam source or a nanofocused nanoparticulate silver ion beam source;

analyzing at least a portion of said sample having the matrix with a fluorescence or Raman spectrometer;

thereafter desorbing chemical species from said sample using a nanofocused primary particle beam source; and, analyzing at least a portion of said desorbed chemical species;

wherein said nanofocused primary particle beam source comprises a nanofocused neon ion particle beam source.

14. The method of claim 13, wherein said step of adding said matrix to said sample with said nanoparticulate beam source comprises adding said matrix with a coreshell structure nanoparticulate beam source comprising a beam source of nanoparticles having a core of a first material surrounded by a shell of a second different material.

15. The method of claim 14, wherein said first material comprises silver and the second material comprises aluminum oxide.

16. The method of claim 13, wherein said nanoparticulate beam source is a nanofocused nanoparticulate beam source of ternary coreshell nanoparticulates.

17. The method of claim 13, further comprising modifying nanoparticulates from said nanoparticulate beam source prior to deposition as a matrix in said sample, such that the nanoparticulate beam source comprises Ag—Al—$Al_2O_3$ ternary coreshells.

* * * * *